US011540728B2

United States Patent
Shute et al.

(10) Patent No.: US 11,540,728 B2
(45) Date of Patent: Jan. 3, 2023

(54) HEART SOUND MEASUREMENT USING MOBILE DEVICES

(71) Applicant: Cardiac Pacemakers, Inc., St. Paul, MN (US)

(72) Inventors: Jonathan B. Shute, Minnetonka, MN (US); Kyle H. Srivastava, St. Paul, MN (US); Pramodsingh H. Thakur, Woodbury, MN (US); Keith R. Maile, New Brighton, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 69 days.

(21) Appl. No.: 16/732,972

(22) Filed: Jan. 2, 2020

(65) Prior Publication Data

US 2020/0214576 A1    Jul. 9, 2020

Related U.S. Application Data (60) Provisional application No. 62/787,911, filed on Jan. 3, 2019.

(51) Int. Cl.
| | | |
|---|---|---|
| *A61B 5/0205* | (2006.01) | |
| *A61B 5/0245* | (2006.01) | |
| *A61B 5/021* | (2006.01) | |
| *A61B 7/04* | (2006.01) | |
| *A61B 5/00* | (2006.01) | |
| *A61B 5/11* | (2006.01) | |

(52) U.S. Cl.
CPC .......... *A61B 5/0205* (2013.01); *A61B 5/1116* (2013.01); *A61B 5/6802* (2013.01); *A61B 5/6847* (2013.01); *A61B 5/6898* (2013.01); *A61B 7/04* (2013.01); *A61B 5/021* (2013.01); *A61B 5/0245* (2013.01)

(58) Field of Classification Search
CPC ... A61B 5/0205; A61B 5/1116; A61B 5/6802; A61B 5/6847; A61B 5/6898; A61B 5/021; A61B 5/0245; A61B 5/686; A61B 5/02405
See application file for complete search history.

(56) References Cited

U.S. PATENT DOCUMENTS

| | | | | |
|---|---|---|---|---|
| 2011/0066042 | A1* | 3/2011 | Pandia | A61B 5/725 |
| | | | | 600/484 |
| 2017/0119273 | A1* | 5/2017 | Thakur | A61B 7/04 |
| 2017/0231508 | A1* | 8/2017 | Edwards | H04J 3/0667 |
| | | | | 600/301 |
| 2018/0344212 | A1* | 12/2018 | An | A61B 5/053 |
| 2018/0368765 | A1* | 12/2018 | Srivastava | A61B 5/021 |

* cited by examiner

*Primary Examiner* — Carl H Layno
*Assistant Examiner* — Aya Ziad Bakkar
(74) *Attorney, Agent, or Firm* — Faegre Drinker Biddle & Reath LLP (57) ABSTRACT

Embodiments of the present disclosure relate to heart sound measurements using mobile devices. In an embodiment, a medical system for monitoring heart sounds of a subject comprises a medical device configured to obtain, during a first sampling interval, a first physiological signal. The medical system further comprises a mobile device comprising an accelerator, wherein the accelerator is configured to obtain, during a second sampling interval, a second physiological signal. And, the medical system comprises an analysis component configured to extract heart sounds data from the second physiological signal.

15 Claims, 5 Drawing Sheets

HEART SOUND MEASUREMENT USING MOBILE DEVICES

CROSS REFERENCE TO RELATED APPLICATION

This application claims priority to Provisional Application No. 62/787,911, filed Jan. 3, 2019, which is herein incorporated by reference in its entirety.

TECHNICAL FIELD

Aspects of this disclosure relate to medical devices and methods for facilitating medical monitoring. More specifically, embodiments relate to medical systems including medical devices configured to communicate with mobile devices, and methods of using such systems.

BACKGROUND

Heart sound can be an important physiological parameter to monitor, particularly with subjects who are at risk of cardiac failure and/or other complications.

SUMMARY

Example embodiments include but are not limited to the following.

In an Example 1, a medical system for monitoring heart sounds of a subject comprises: a medical device configured to obtain, during a first sampling interval, a first physiological signal; and a mobile device comprising an accelerator, wherein the accelerator is configured to obtain, during a second sampling interval, a second physiological signal; an analysis component configured to extract heart sounds data from the second physiological signal.

In an Example 2, the medical system of claim 1, wherein the analysis component is further configured to determine, based on the heart sounds data, at least one of heart rate, heart rate variability (HRV), and blood pressure.

In an Example 3, the medical system of either of claim 1 or 2, wherein the analysis component is implemented in the medical device and/or the mobile device, and is further configured to: detect a quiet period, wherein the quiet period comprises a period of time that has a length that exceeds a specified threshold and during which an activity level of the subject satisfies a specified quiet condition; and cause, in response to detecting the quiet period, the mobile device to obtain the second physiological signal.

In an Example 4, the medical system of any of claim 1-3, further comprising a posture sensor implemented in the medical device and/or the mobile device, wherein the posture sensor is configured to determine a posture of the subject during the second sampling interval and provide an indication of the determined posture to the analysis component.

In an Example 5, the medical system of any of claims 1-4, wherein the analysis component is configured to extract heart sounds data from the second physiological signal by: receiving the second physiological signal; applying a heart sounds filter to the second physiological signal to create a filtered second physiological signal; applying a temporal filter to the second physiological signal to determine a temporal window corresponding to a beat; identify signal peaks within the temporal window; extract, from the filtered physiological signal, acceleration data corresponding to the identified signal peaks; and determine, from the extracted acceleration data, the heart sounds data.

In an Example 6, the medical system of claim 5, wherein the analysis component is configured to determine the heart sounds data by identifying approximate heart sounds locations based on a template and cross-correlating a plurality of extracted beats to the template.

In an Example 7, the medical system of any of claims 1-6, wherein the analysis component is further configured to: determine a first timing fiducial and a second timing fiducial; determine a difference between the first timing fiducial and the second timing fiducial; and determine, based on the difference, a blood pressure measurement.

In an Example 8, the medical system of any of claims 1-7, wherein the medical device is an implantable medical device.

In an Example 9, the medical system of any of claims 1-7, wherein the medical device is a wearable medical device.

In an Example 10, the medical system of any of claims 1-9, further comprising a support device configured to communicate with the medical device and the mobile device, and synchronizes the medical device and the mobile device to a global resolution clock.

In an Example 11, a method of monitoring heart sounds of a subject comprises: receiving a physiological signal obtained by a mobile device; applying a heart sounds filter to the physiological signal to create a filtered physiological signal; applying a temporal filter to the physiological signal to determine a temporal window corresponding to a beat; identifying signal peaks within the temporal window; extracting, from the filtered physiological signal, acceleration data corresponding to the identified signal peaks; and determining, from the extracted acceleration data, heart sounds data.

In an Example 12, the method of claim 11, wherein determining the heart sounds data comprises: identifying approximate heart sounds locations based on a template; and cross-correlating a plurality of extracted beats to the template.

In an Example 13, the method of either of claim 11 or 12, further comprising: determining a first timing fiducial and a second timing fiducial, wherein the first timing fiducial corresponds to a first beat extracted from a physiological signal obtained by a medical device, and wherein the second timing fiducial corresponds to a second beat extracted from the physiological signal obtained by the mobile device; determining a difference between the first timing fiducial and the second timing fiducial; and determining, based on the difference, a blood pressure measurement.

In an Example 14, the method of any of claims 11-13, further comprising: detecting a quite period, wherein the quiet period comprises a period of time that has a length that exceeds a specified threshold and during which an activity level of the subject satisfies a specified quiet condition; and causing, in response to detecting the quiet period, the mobile device to obtain the second physiological signal.

In an Example 15, the method of claim 13, wherein the medical device is an implantable medical device.

In an Example 16, a medical system for monitoring heart sounds of a subject comprises: a medical device configured to obtain, during a first sampling interval, a first physiological signal; and a mobile device comprising an accelerator, wherein the accelerator is configured to obtain, during a second sampling interval, a second physiological signal; an analysis component configured to extract heart sounds data from the second physiological signal.

In an Example 17, the medical system of claim 16, wherein the analysis component is further configured to determine, based on the heart sounds data, at least one of heart rate, heart rate variability (HRV), and blood pressure.

In an Example 18, the medical system of claim 16, wherein the analysis component is implemented in the medical device and/or the mobile device, and is further configured to: detect a quiet period, wherein the quiet period comprises a period of time that has a length that exceeds a specified threshold and during which an activity level of the subject satisfies a specified quiet condition; and cause, in response to detecting the quiet period, the mobile device to obtain the second physiological signal.

In an Example 19, the medical system of claim 16, further comprising a posture sensor implemented in the medical device and/or the mobile device, wherein the posture sensor is configured to determine a posture of the subject during the second sampling interval and provide an indication of the determined posture to the analysis component.

In an Example 20, the medical system of claim 16, wherein the analysis component is configured to extract heart sounds data from the second physiological signal by: receiving the second physiological signal; applying a heart sounds filter to the second physiological signal to create a filtered second physiological signal; applying a temporal filter to the second physiological signal to determine a temporal window corresponding to a beat; identify signal peaks within the temporal window; extract, from the filtered physiological signal, acceleration data corresponding to the identified signal peaks; and determine, from the extracted acceleration data, the heart sounds data.

In an Example 21, the medical system of claim 20, wherein the analysis component is configured to determine the heart sounds data by identifying approximate heart sounds locations based on a template and cross-correlating a plurality of extracted beats to the template.

In an Example 22, the medical system of claim 16, wherein the analysis component is further configured to: determine a first timing fiducial and a second timing fiducial; determine a difference between the first timing fiducial and the second timing fiducial; and determine, based on the difference, a blood pressure measurement.

In an Example 23, the medical system of claim 16, wherein the medical device is an implantable medical device.

In an Example 24, the medical system of claim 16, wherein the medical device is a wearable medical device.

In an Example 25, the medical system of claim 16, further comprising a support device configured to communicate with the medical device and the mobile device, and synchronizes the medical device and the mobile device to a global resolution clock.

In an Example 26, a method of monitoring heart sounds of a subject comprises: receiving a physiological signal obtained by a mobile device; applying a heart sounds filter to the physiological signal to create a filtered physiological signal; applying a temporal filter to the physiological signal to determine a temporal window corresponding to a beat; identifying signal peaks within the temporal window; extracting, from the filtered physiological signal, acceleration data corresponding to the identified signal peaks; and determining, from the extracted acceleration data, heart sounds data.

In an Example 27, the method of claim 26, wherein determining the heart sounds data comprises: identifying approximate heart sounds locations based on a template; and cross-correlating a plurality of extracted beats to the template.

In an Example 28, the method of claim 26, further comprising: determining a first timing fiducial and a second timing fiducial, wherein the first timing fiducial corresponds to a first beat extracted from a physiological signal obtained by a medical device, and wherein the second timing fiducial corresponds to a second beat extracted from the physiological signal obtained by the mobile device; determining a difference between the first timing fiducial and the second timing fiducial; and determining, based on the difference, a blood pressure measurement.

In an Example 29, the method of claim 26, further comprising: detecting a quite period, wherein the quiet period comprises a period of time that has a length that exceeds a specified threshold and during which an activity level of the subject satisfies a specified quiet condition; and causing, in response to detecting the quiet period, the mobile device to obtain the second physiological signal.

In an Example 30, the method of claim 26, wherein the medical device is an implantable medical device.

In an Example 31, one or more computer-readable media having computer-executable instructions embodied thereon that, when executed by at least one processor, cause the at least one processor to instantiate at least one program component, the at least one program component comprising an analysis component, the analysis component configured to: receive a physiological signal obtained by a mobile device; and extract heart sounds data from the physiological signal.

In an Example 32, the media of claim 31, wherein the analysis component is configured to extract heart sounds data from the physiological signal by: applying a heart sounds filter to the physiological signal to create a filtered physiological signal; applying a temporal filter to the physiological signal to determine a temporal window corresponding to a beat; identify signal peaks within the temporal window; extract, from the filtered physiological signal, acceleration data corresponding to the identified signal peaks; and determine, from the extracted acceleration data, the heart sounds data.

In an Example 33, the media of claim 31, wherein the analysis component is further configured to: determine a first timing fiducial and a second timing fiducial, wherein the first timing fiducial corresponds to a first beat extracted from a physiological signal obtained by a medical device, and wherein the second timing fiducial corresponds to a second beat extracted from the physiological signal obtained by the mobile device; determine a difference between the first timing fiducial and the second timing fiducial; and determine, based on the difference, a blood pressure measurement.

In an Example 34, the media of claim 33, wherein the medical device is an implantable medical device.

In an Example 35, the media of claim 33, wherein the medical device is a wearable medical device.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Embodiments of the subject matter disclosed herein facilitate obtaining heart sounds data using a mobile device such as a cell phone, which may be disposed in the subject's pocket. In embodiments, for example, the accelerometer of a subject's mobile device may be used to obtain heart sounds data, which may, in turn, be used to calculate pulse transit times with respect to an implanted or wearable medical device. Pulse transit time can be used to determine a measure of blood pressure. Other parameters such as heart rate and heart rate variability (HRV) may also be determined. In this manner, for example, a recipient of a cardiac monitoring device may be able to add an app to his or her cell phone that would be configured to utilize the accelerometer of the phone to offer aspects of the functionality discussed herein.

Embodiments of the subject matter disclosed herein may be further configured to enable a neuromodulation device (e.g., an external programmer) to obtain heart sounds measurements that can be used to enhance the effectiveness of certain types of neuromodulation therapy. Additionally, or alternatively, the ability to measure heart sounds using a mobile device may facilitate identifying potential cardiac concerns in subjects, thereby providing a mechanism to identify candidates for receiving an implantable cardiac monitor.

Figure 1:
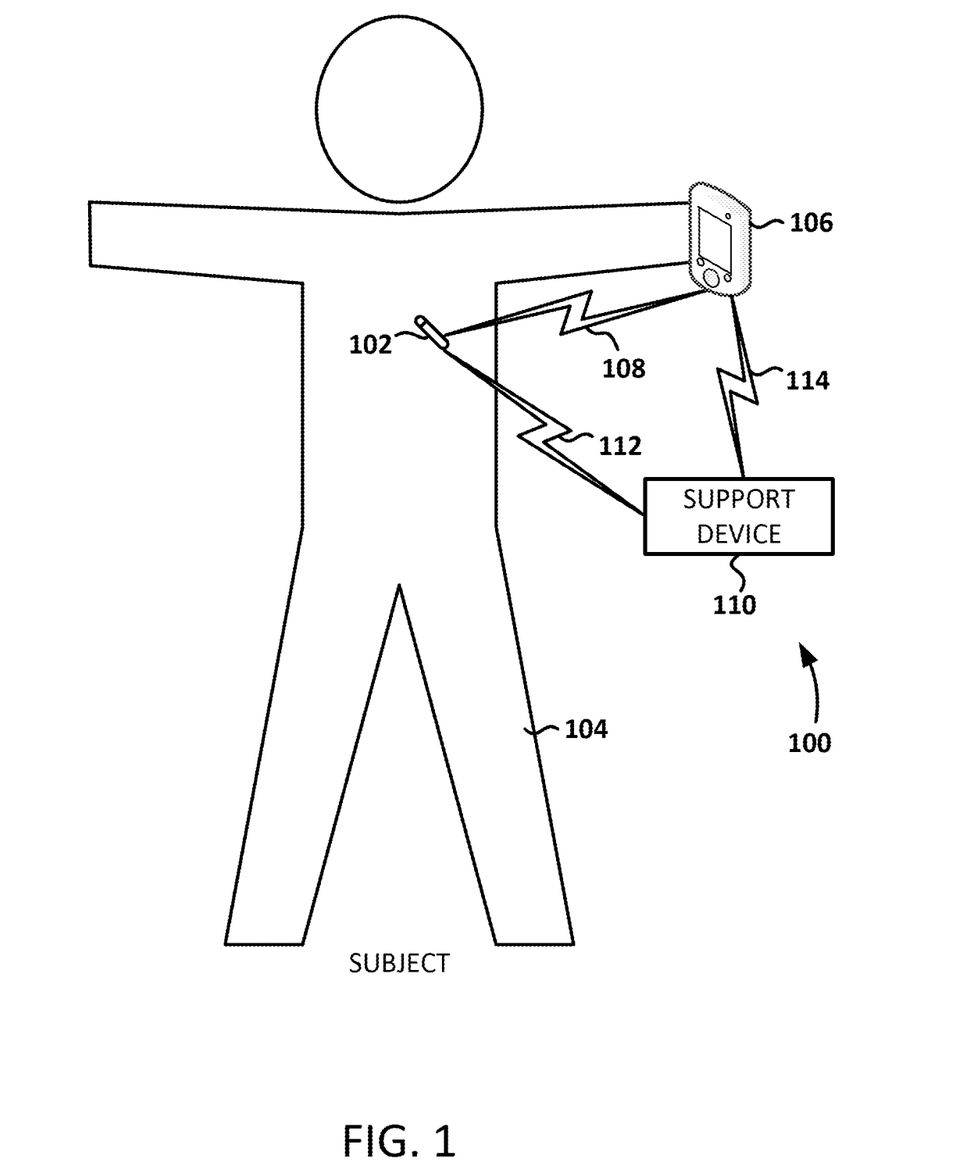
FIG. 1 is a schematic illustration of a medical system including a medical device and a mobile device, in accordance with embodiments of the disclosure.

FIG. 1 shows an illustrative medical system 100, in accordance with embodiments of the disclosure. As shown in FIG. 1, the medical system 100 includes a medical device 102 configured to be operatively connected to the body of a subject 104, and a mobile device 106, which is communicatively coupled to the medical device 102 via a communication link 108. The medical system 100 may further include a support device 110, which may be communicatively coupled to the medical device 102 via a communication link 112 and/or to the mobile device 106 via a communication link 114. The subject 104 may be a human, a dog, a pig, and/or any other animal having physiological parameters that can be recorded. For example, in embodiments, the subject 104 may be a human patient.

In embodiments, any one or more of the communication links 108, 112, and 114 may be, or include, a wireless communication link such as, for example, a short-range radio link, such as Bluetooth, IEEE 802.11, a proprietary wireless protocol, and/or the like. In embodiments, for example, one or more of the communication links 108, 112, and 114 may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, one or more of the communication links 108, 112, and 114 may be, or include, a persistent communication link, an intermittent communication link, an ad-hoc communication link, and/or the like. One or more of the communication links 108, 112, and 114 may refer to direct communications between the linked devices, and/or indirect communications that travel between the linked devices via at least one other device (e.g., a repeater, router, hub, and/or the like). One or more of the communication links 108, 112, and 114 may facilitate uni-directional and/or bi-directional communication between the linked devices. Data and/or control signals may be transmitted between the linked devices to coordinate the functions thereof. In embodiments, patient data may be downloaded from one or more of the medical device 102, the mobile device 106, and the support device 110, periodically or on command. The physician and/or the subject may communicate with the medical device 102, the mobile device 106, and/or the support device 110, for example, to acquire patient data or to initiate, terminate and/or modify recording and/or therapy.

In embodiments, the medical device 102 and/or the mobile device 106 may provide one or more of the following functions with respect to a patient: sensing, data analysis, and therapy. For example, in embodiments, the medical device 102 and/or the mobile device 106 may be used to measure any number of a variety of physiological, device, subjective, and/or environmental parameter signals associated with the subject 104, using electrical, mechanical, and/or chemical means. The medical device 102 and/or the mobile device 106 may be configured to automatically gather data, gather data upon request (e.g., input provided by the subject, a clinician, another device, and/or the like), and/or any number of various combinations and/or modifications thereof. The medical device 102 and/or the mobile device 106 may be configured to compress and/or store data related to the physiological, device, environmental, and/or subjective parameter signals and/or transmit the data to any number of other devices in the system 100. In embodiments, the medical device 102 and/or the mobile device 106 may be configured to analyze data and/or act upon the analyzed data. For example, the medical device 102 and/or the mobile device 106 may be configured to modify therapy, perform additional monitoring, and/or provide alarm indications based on the analysis of the data.

According to embodiments, the medical device 102 may include any number of different types of medical devices, any number of different components of an implantable and/or external system, and/or the like. For example, the medical device 102 may include an implantable medical device (IMD), an external medical device (e.g., a worn medical device), and/or the like. That is, for example, in embodiments, the medical device 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the IMD 102. In various embodiments, the IMD 102 may include both defibrillation and pacing/CRT capabilities (e.g., a CRT-D device).

In embodiments, the medical device 102 may be implanted subcutaneously within an implantation location or pocket in the subject's chest or abdomen and may be configured to monitor (e.g., sense and/or record) physiological parameters associated with the subject's heart. In embodiments, the medical device 102 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In addition, the medical device 102 may be configured to detect a variety of physiological signals that may be used in connection with various diagnostic, therapeutic and/or monitoring implementations. For example, the medical device 102 may include sensors or circuitry for detecting respiratory system signals, cardiac system signals, heart sounds, and/or signals related to patient activity. In embodiments, the medical device 102 may be configured to sense intrathoracic impedance, from which various respiratory parameters may be derived, including, for example, respiratory tidal volume and minute ventilation. Sensors and associated circuitry may be incorporated in connection with the medical device 102 for detecting one or more body movement or body posture and/or position related signals. For example, accelerometers and/or GPS devices may be employed to detect patient activity, patient location, body orientation, and/or torso position.

Derived parameters may also be monitored using the medical device 102. For example, a sleep sensor may rely on measurements taken by an implanted accelerometer that measures body activity levels. The sleep sensor may estimate sleeping patterns based on the measured activity levels. Other derived parameters include, but are not limited to, a functional capacity indicator, autonomic tone indicator, sleep quality indicator, cough indicator, anxiety indicator, and a cardiovascular wellness indicator for calculating a quality of life indicator quantifying a subject's overall health and well-being.

In various embodiments, the medical device 102 and/or the support device 110 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. For example, the medical device 102 and/or the support device 110 may be, or include, a wearable cardiac defibrillator (WCD) such as a vest that includes one or more defibrillation electrodes. In embodiments, the medical device 102 and/or the support device 110 may include any number of different therapy components such as, for example, a defibrillation component, a drug delivery component, a neurostimulation component, a neuromodulation component, a temperature regulation component, and/or the like.

In embodiments, the support device 110 may include sensing components such as, for example, one or more surface electrodes configured to obtain an electrocardiogram (ECG), one or more accelerometers configured to detect motion associated with the patient 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the patient 104, and/or the like. In embodiments, the support device 110 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

In embodiments, the medical device 102, the mobile device 106, and/or the support device 110 may be configured to monitor physiological parameters that may include one or more signals indicative of a patient's physical activity level and/or metabolic level, such as an acceleration signal. In embodiments, the medical device 102, the mobile device 106, and/or the support device 110 may be configured to sense intrathoracic impedance, from which various respiratory parameters may be derived, including, for example, respiratory rate, tidal volume and minute ventilation. Sensors and associated circuitry may be incorporated in connection with the medical device 102, the mobile device 106, and/or the support device 110 for detecting one or more body movement or body posture and/or position related signals. For example, accelerometers, gyroscopes, and/or GPS devices may be employed to detect patient activity, patient location, body orientation, and/or torso position. The medical device 102, the mobile device 106, and/or the support device 110 may be configured to sense and/or record at regular intervals, continuously, and/or in response to a detected event.

Although not explicitly shown in FIG. 1, the system 100 may include any number of external communication devices, programmers, servers, and/or the like. In embodiments, the support device 110 may be, include, or be included in, a communication device, programmer, server, and/or the like. According to embodiments, an external communication device and/or a programmer may be configured to send data to, and receive data from, a device, such as the medical device 102, the mobile device 106, the support device 110, and/or any number of other devices depicted or not depicted in FIG. 1. In this manner, for example, embodiments may include a server that may be used to perform analysis on data received from one or more of the other devices in the system 100. Such communications may be facilitated via any number of communication links, any number of which may be, be identical to, be similar to, include, be coupled with, or be included within, one or more of the communication links 108, 112, and 114.

In embodiments, the system 100 may be configured to monitor heart sounds of a subject such as, for example, by extracting heart sounds data from physiological signals measured at two or more different locations. In this manner, for example, the system may use heart sound data collected using a cell phone or other similar consumer mobile device to determine heart rate, heart rate variability, pulse transit time between the cell phone and the medical device (e.g., to determine blood pressure), and/or the like. For example, in embodiments, the system may be configured to determine a first timing fiducial and a second timing fiducial, where the first timing fiducial corresponds to a first beat extracted from a physiological signal obtained by a medical device, and where the second timing fiducial corresponds to a second beat extracted from the physiological signal obtained by the mobile device; determine a difference between the first timing fiducial and the second timing fiducial; and determine, based on the difference, a blood pressure measurement.

The medical device 102 may be configured to monitor physiological parameters that may include one or more signals indicative of a patient's physical activity level and/or metabolic level, such as an acceleration signal. In embodiments, the medical device 102 may be configured to monitor physiological parameters associated with one or more other organs, systems, and/or the like. The medical device 102 may be configured to sense and/or record at regular intervals, continuously, and/or in response to a detected event. For example, according to embodiments, the medical device 102 may be configured to detect a trigger event and perform an action in response to detecting the trigger event and/or communicate a notification of the trigger event to the mobile device 106, which may perform one or more actions in response.

For example, the medical device 102 may be configured to detect a quiet period, wherein the quiet period includes a period of time that has a length that exceeds a specified threshold and during which an activity level of the subject satisfies a specified quiet condition. That is, for example, the medical device 102 may include a patient activity level sensor, which may be or include an accelerometer, GPS component, inertial measuring unit (IMU), and/or the like, that may be configured to determine an activity level of the patient. If the activity level of the patient stays, for example, at or below a specified threshold for at least a specified amount of time, the medical device 102 may be configured to provide a communication to the mobile device 106 that causes the mobile device to obtain a physiological signal (e.g., a signal from which heart sound data can be extracted). Other trigger events may include, for example, a particular posture of the subject, a time of day, a specified environmental condition, and/or the like.

Additionally, or alternatively, the mobile device 106 may be configured to detect the trigger event. In embodiments, in response to detection of the trigger event (e.g., by the medical device 102 and/or the mobile device 106), the medical device 102 may be configured to obtain, during a first sampling interval, a first physiological signal, and the mobile device 106 may be configured to obtain, during a second sampling interval, a second physiological signal. The medical device 102 and/or the mobile device 106 may be configured to manage the timing of the two sampling intervals, e.g., by communicating with the other device to synchronize the timing of the sampling intervals, by sending a communication to the other device that causes the receiving device to obtain the respective physiological signal at a certain time, and/or the like.

According to embodiments, the synchronization of the medical device 102 and the mobile device 106 with respect to the sampling intervals may be performed by the support device 110, which may synchronize the devices according to a global resolution clock (e.g., an independent clocking mechanism that tracks a single time to be used as a reference by which the sampling intervals can be scheduled. In embodiments the support device 110 may be an independent device such as, for example, a docking station, a mobile device, a programmer, and/or the like. In embodiments, the support device 110 may be integrated with the medical device 102 and/or the mobile device 106.

That is, for example, upon receiving the communication from the medical device 102, the mobile device 106 may activate an accelerometer, which obtains a physiological signal—that is, acceleration data associated with a location on the subject for a specified time interval. For example, the mobile device 106, which may be a smartphone, may be disposed in a pocket of the subject's pants. In embodiments, the mobile device 106 may be a wearable device such as, for example, a watch (e.g., disposed on the subject's wrist), a bracelet, an anklet, a device embedded in an article of clothing or an accessory (e.g., a belt, necklace, etc.), and/or the like.

The illustrative medical system 100 shown in FIG. 1 is not intended to suggest any limitation as to the scope of use or functionality of embodiments of the present disclosure. The illustrative system 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
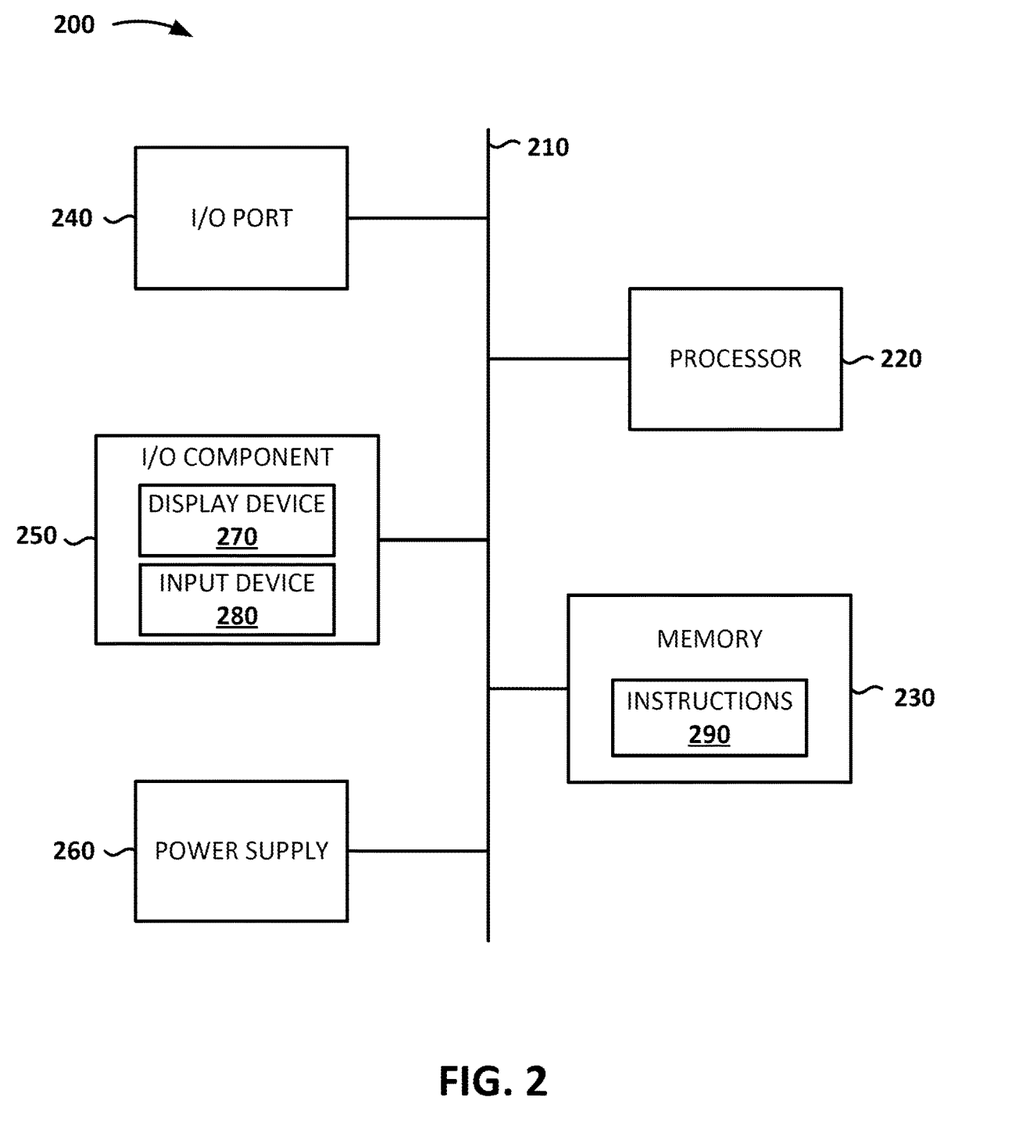
FIG. 2 is a block diagram of a computing device, in accordance with embodiments of the disclosure.

According to various embodiments of the disclosed subject matter, any number of the components depicted in FIG. 1 (e.g., the mobile device 106, the support device 110, etc.) may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device 270, a speaker, a printing device, and/or the like, and/or an input device 280 such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 290 for causing the processor 220 to implement aspects of embodiments of system components discussed herein and/or to perform aspects of embodiments of methods and procedures discussed herein.

The computer-executable instructions 290 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. The illustrative computing device 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
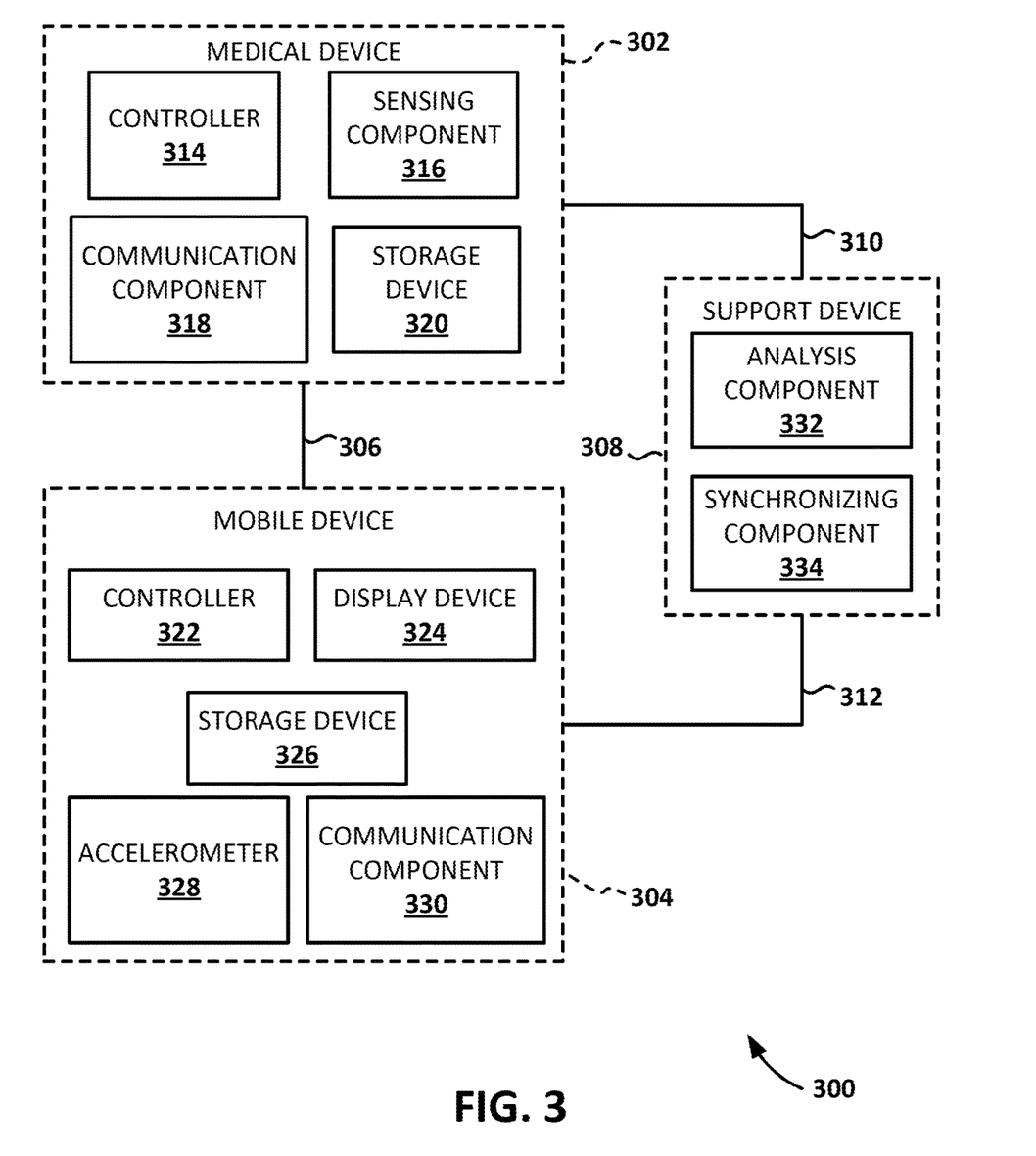
FIG. 3 is a block diagram of a medical system having a medical device and a mobile device, in accordance with embodiments of the disclosure.

FIG. 3 is a block diagram depicting an illustrative medical system 300, in accordance with embodiments of the disclosure. As shown, the system 300 includes a medical device 302 and a mobile device 304 configured to communicate with one another via a communication link 306. Embodiments of the system may include more than one medical device 302 and/or more than one mobile device 304. As shown, embodiments also include a support device 308. The support device 308 may be configured to communicate with the medical device 302 via a communication link 310, and/or with the mobile device 304 via a communication link 312. The medical device 302 may be, be similar, to, include, or be included in, the medical device 102 depicted in FIG. 1; the mobile device 304 may be, be similar to, include, or be included in, the mobile device 106 depicted in FIG. 1; and the support device 308 may be, be similar to, include, or be included in, the support device 110 depicted in FIG. 1.

According to embodiments illustrated in FIG. 3, the medical device 302 includes a controller 314, a sensing component 316, a communication component 318, and a storage device 320. The controller 314 may include, for example, a processing unit, a pulse generator, and/or the like. The controller 314 may be any arrangement of electronic circuits, electronic components, processors, program components and/or the like configured to store and/or execute programming instructions, to direct the operation of the other functional components of the medical device 302, to perform arrhythmia detection and/or classification algorithms, to perform ultrasound imaging tasks (e.g., identification of B-lines for diagnosing and/or confirming pulmonary edema), to store physiologic data obtained by the sensing component 316, and/or the like, and may be implemented, for example, in the form of any combination of hardware, software, and/or firmware.

In embodiments, the controller 314 may be a programmable micro-controller or microprocessor, and may include one or more programmable logic devices (PLDs) or application specific integrated circuits (ASICs). In some implementations, the controller 314 may include memory as well. Although embodiments of the present system 300 are described in conjunction with a medical device 302 having a processor-based architecture, it will be understood that the medical device 302 (or other device) may be implemented in any logic-based integrated circuit architecture, if desired. The controller 308 may include digital-to-analog (D/A) converters, analog-to-digital (N/D) converters, timers, counters, filters, switches, and/or the like. The controller 308 may execute instructions and perform desired tasks as specified by the instructions.

The controller 308 may also be configured to store information in the storage device 320 and/or access information from the storage device 320. The storage device 320 may be, be similar to, include, or be included within, the memory 230 depicted in FIG. 2. That is, for example, the storage device 320 may include volatile and/or non-volatile memory, and may store instructions that, when executed by the controller 308 cause methods and processes to be performed by the medical device 302. In embodiments, the controller 308 may process instructions and/or data stored in the medical device 302 to control sensing operations performed by the medical device 302, to control communications performed by the medical device 302, and/or the like. For example, the controller 308 may include a processing component configured to process a sensed signal, e.g., to determine parameters, derived features, and/or the like.

The medical device 302 may sense physiological parameter signals using a sensing component 316 that may include, for example, one or more sensors, one or more medical devices, or a combination of these. In embodiments, the sensing component 316 may include any number of electrical circuits, electronic components, processors, program components and/or the like. The storage device 320 may be used to store sensed information according to some implementations. Information from sense circuits included in the sensing component 316 may be used to adjust therapy, sensing, and/or communications parameters.

In embodiments, the sensing component 316 may be configured to sense intrinsic cardiac electrical signals in a manner similar to known electrocardiogram (ECG) electrodes, which signals are transmitted via conventional techniques to the controller 308. In various embodiments, the sensing component 316 may be configured to sense other patient physiologic or environmental parameters in addition to, or alternative to, cardiac signals. In embodiments, the sensing component 316 may include temperature sensors (e.g., thermocouples or thermistors), barometers, acoustic transducers, pressure sensors, optical sensors, motion or impact sensors (e.g., accelerometers, inertial measuring units (IMUs)), strain sensors, posture sensors, Doppler systems, ultrasound sensors, and/or the like, in any number of various types of configurations. The foregoing sensors allow the medical device 302 to be capable of sensing and recording physiologic parameters such as, for example, patient movement, posture, respiratory rate and/or volume, heart sounds, impedance, fluid levels, and/or the like. The output from the sensing component 316 may be used in arrhythmia detection and classification, pulmonary edema diagnosis and/or confirmation, therapy selection, and/or the like. Additionally or alternatively, the output from the sensing component 316 may be used in heart sound monitoring and may include, or example, heart sound data.

The communication component 318 may include, for example, circuits, program components, and one or more transmitters and/or receivers for communicating wirelessly with one or more other devices such as, for example, the mobile device 304. According to various embodiments, the communication component 318 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 318 may include any combination of hardware, software, and/or firmware configured to facilitate establishing, maintaining, and using any number of communication links.

As indicated above, the mobile device 304 may be, include, or be included in a consumer mobile device such as, for example, a cell phone (e.g., a smartphone), a personal digital assistant (PDA), a tablet computer, a watch, a bracelet, an anklet, patch, a belt, a garment, and/or the like. As shown in FIG. 3, the mobile device 304 includes a controller 322, a display device 324, a storage device 326, an accelerometer 328, and a communication component 330. In embodiments, the accelerometer 328 and/or communication component 330 may be implemented in any combination of hardware, software, and/or firmware, and may be implemented, at least in part, by the controller 322. The controller 322 may be any suitable controller 322 configured for implementation in a mobile device and may be identical to, or similar to, the controller 314 of the medical device 302.

Additionally, the storage device 326 and communication component 330 may be identical to, or similar to, the storage device 320 and the communication component 318, respectively, of the medical device 302. That is, for example, the storage device 326 may include volatile and/or non-volatile memory, and may store instructions that, when executed by the controller 322 cause methods and processes to be performed by the mobile device 304. In embodiments, the controller 322 may process instructions and/or data stored in the storage device 326 to control communications performed by the communication component 330. The mobile device 304 may include any number of other components or combination of components including, for example, an analysis component, a sensing component, a therapy component, and/or the like.

According to embodiments, the accelerometer 328 may be any type of accelerometer known in the art as being implemented in a mobile device such as a cellphone, and may be configured to obtain acceleration data, e.g, as a physiological signal. For example, the inventors have found that such an accelerometer is capable of obtaining a physiological signal having hear sound data therein if the mobile device is placed against the subject's thigh, even with clothing disposed between the mobile device and the skin. In embodiments, a specialty accelerometer may be designed and implemented.

As is shown in FIG. 3, embodiments of the system 300 include the support device 308. According to embodiments, the support device may be, be similar to, include, or be included in the support device 110 depicted in FIG. 1. In embodiments, one or more aspects of the support device 308 may be integrated with the medical device 302 and/or the mobile device 304. In embodiments, one or more aspects of the support device 308 may be implemented in a separate device such as, for example, a communication hub, a programmer, a server, a docking station, and/or the like. As shown, the support device includes an analysis component 332 and a synchronizing component 334. As indicated above, the analysis component 332, or any aspect thereof, may be implemented on any number of different devices in the system 300 such as, for example, the medical device 302, the mobile device 304, the support device 308, and/or the like. Similarly, the synchronizing component 334, or any aspect thereof, may be implemented on any number of different devices in the system 300 such as, for example, the medical device 302, the mobile device 304, the support device 308, and/or the like.

According to embodiments, the analysis component 332 may be implemented using any number of different combinations of hardware, software, and/or firmware. According to embodiments, the analysis component 332 may be configured to extract heart sounds data from a physiological signal obtained by a mobile device. In embodiments, the analysis component 332 may be further configured to determine, based on the heart sounds data, at least one of heart rate, heart rate variability (HRV), and blood pressure.

In embodiments, the analysis component 332 is implemented in the medical device and/or the mobile device, and is further configured to: detect a quiet period, where the quiet period includes a period of time that has a length that exceeds a specified threshold and during which an activity level of the subject satisfies a specified quiet condition. In embodiments, the specified time threshold and specified quiet condition may be any number of different values, ranges, and/or the like. The analysis component 332 may be further configured to cause, in response to detecting the quiet period, the mobile device to obtain the second physiological signal.

According to embodiments, the analysis component 332 may be configured to engage in any number of different types of analysis. In embodiments, the analysis component 332 may be configured to extract heart sounds data from the second physiological signal by using a repetitive morphology analysis. For example, in embodiments, the analysis component 332 may be configured to receive the second physiological signal, apply a heart sounds filter to the second physiological signal to create a filtered second physiological signal; and apply a temporal filter to the second physiological signal to determine a temporal window corresponding to a beat. According to embodiments, the heart sound filter may include, for example, a frequency filter that filters out all frequencies except frequencies associated with heart sounds (e.g., frequencies of approximately 10 to approximately 90 hertz). The temporal filter may be used for beat localization and may be configured to let signals having frequencies of between approximately 0.5 and 2 hertz. In embodiments, the analysis component 332 may be configured to apply these filters in parallel—that is, by forking the incoming signal to the two filters independently.

The analysis component 332 may be further configured to identify signal peaks within the temporal window; extract, from the filtered physiological signal, acceleration data corresponding to the identified signal peaks; and determine, from the extracted acceleration data, the heart sounds data. In embodiments, the peaks of the extracted heart sounds data may be used to identify a pulse transit time. According to embodiments, the analysis component may be configured to determine the heart sounds data by identifying approximate heart sounds locations based on a template and cross-correlating a plurality of extracted beats to the template. For example, in embodiments, the analysis component may be configured to apply a heart sounds template to identify the beat with a highest energy level at sample 40 and the beat with the lowest energy level at sample 5. Cross-correlating the beats to the template may involve using ensemble averaging to increase the signal-to-noise ratio.

According to embodiments, obtaining signals may be conditioned upon the occurrence of trigger events such as, for example, the detection of a quiet period, the subject having a certain posture, and/or the like. In embodiments, the data associated with these trigger events may additionally, or alternatively, be utilized by the analysis component 332 to facilitate refining the analysis. For example, data associated with activity of the subject may be used to filter artifacts from the physiological signals that arise as a result of that activity. Additionally, data associated with the posture of the subject may be used to estimate a quality of coupling between the accelerometer in the mobile device and the subject. In embodiments, the analysis component 332 may be configured to cause, in response to detecting a coupling quality that fails to satisfy a predetermined threshold, an indication to be displayed (or otherwise conveyed) to a user, such as the subject. In embodiments, the indication may be accompanied by an instruction to be followed to facilitate improving the coupling quality. For example, the instruction might instruct the subject to place the mobile device 304 into a particular pocket, to lay down, to reduce the subject's activity, and/or the like.

According to embodiments, the analysis may be further refined by using an external global resolution clock to synchronize the medical device 302 sampling interval and the mobile device 304 sampling interval, which may be used to further refine the peak detection process, the beat localization, and/or the like. The synchronizing component 334 may be configured to communicate with the medical device 302 and the mobile device 304, and may facilitate synchronizes the medical device and the mobile device to a global resolution clock.

The illustrative medical system 300 shown in FIG. 3 is not intended to suggest any limitation as to the scope of use or functionality of embodiments of the present disclosure. The illustrative medical system 300 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
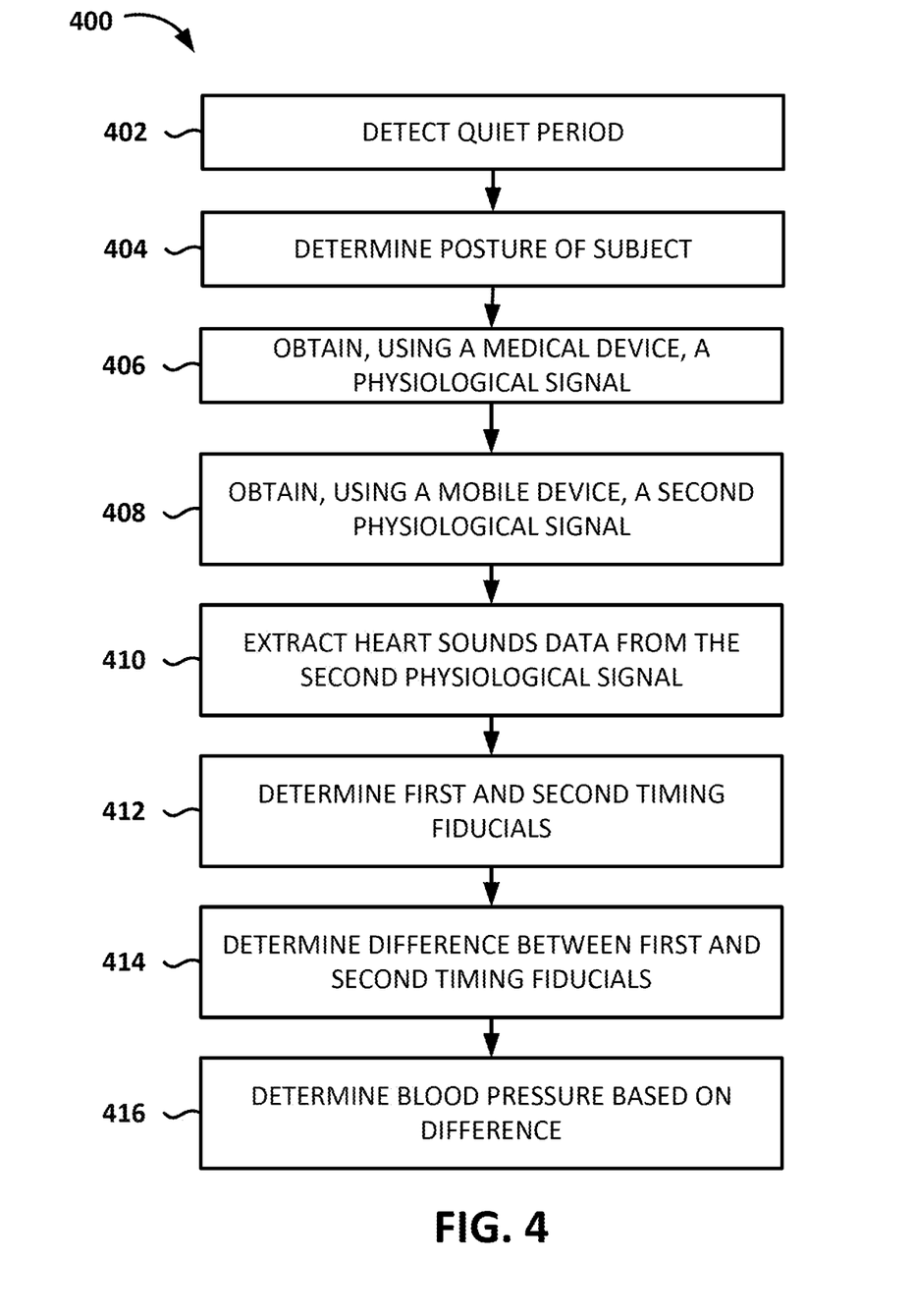
FIG. 4 is a flow diagram illustrating a method of monitoring heart sounds of a subject, in accordance with embodiments of the disclosure.

FIG. 4 is a flow diagram depicting an illustrative method 400 of monitoring heart sounds of a subject, using a medical system in accordance with embodiments of the disclosure. According to embodiments, the medical system may be, be similar to, include, or be included in, the medical system 100 depicted in FIG. 1, and/or the medical system 300 depicted in FIG. 3. Embodiments of the method 400 include detecting a quiet period, where the quiet period includes a period of time that has a length that exceeds a specified threshold and during which an activity level of the subject satisfies a specified quiet condition (block 402); and determining a posture of the subject (block 404).

Embodiments of the method 400 further include obtaining, using a medical device, a first physiological signal (block 406) and obtaining, using a mobile device, a second physiological signal (block 408). In embodiments, the first and/or second physiological signals may be obtained in response to detecting the quiet period and/or determining the posture of the subject. Embodiments of the method 400 further include extracting heart sounds data from the second physiological signal (block 410). As is shown in FIG. 4, the method 400 may also include determining a first timing fiducial and a second timing fiducial (block 412); determining a difference between the first timing fiducial and the second timing fiducial (block 414); and determining, based on the difference, a blood pressure measurement (block 416), which may be inversely related to the difference.

Figure 5:
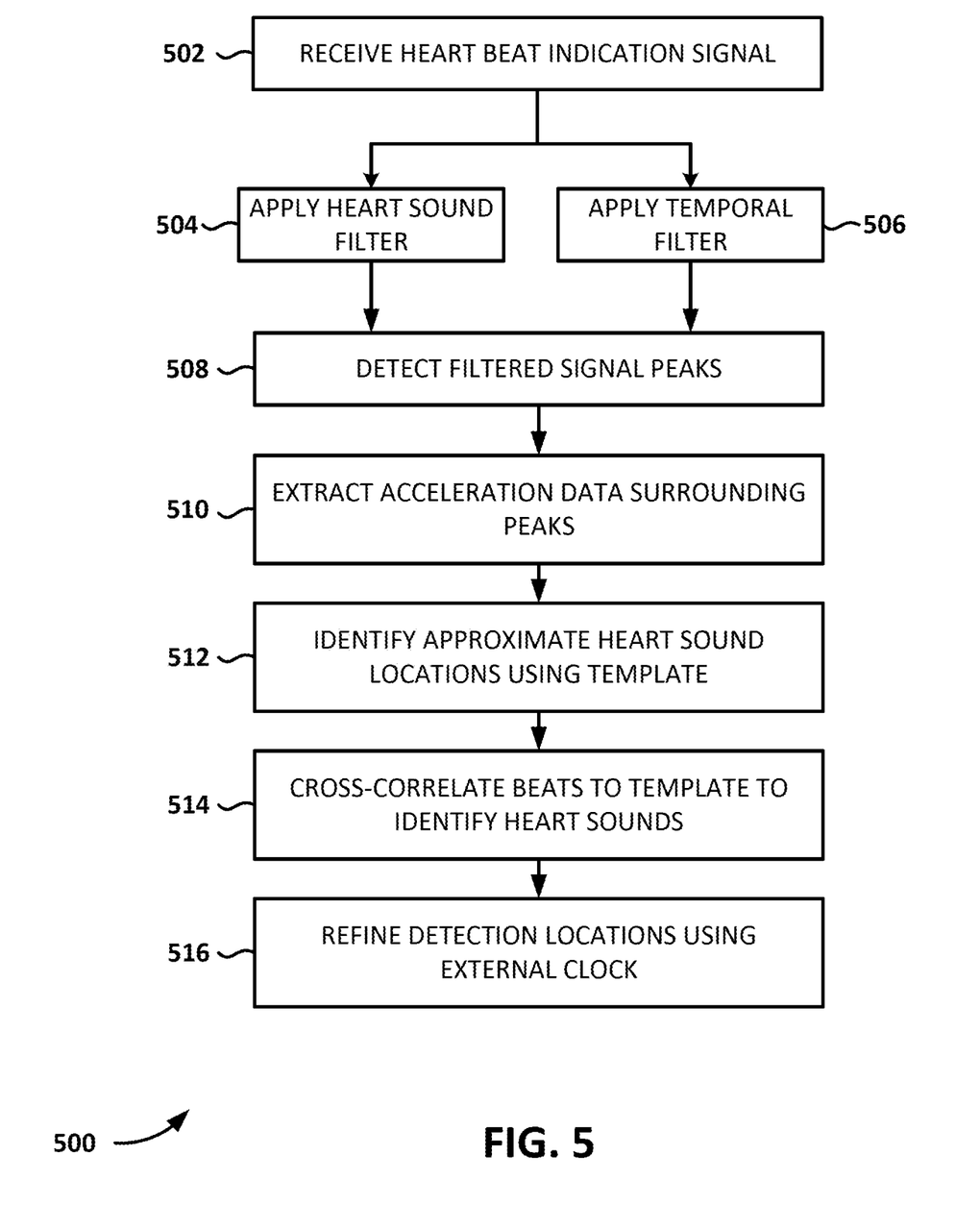
FIG. 5 is a flow diagram illustrating a method of monitoring heart sounds of a subject, in accordance with embodiments of the disclosure.

FIG. 5 is a flow diagram depicting an illustrative method 500 of monitoring heart sounds of a subject, using a medical system in accordance with embodiments of the disclosure. According to embodiments, the medical system may be, be similar to, include, or be included in, the medical system 100 depicted in FIG. 1, and/or the medical system 300 depicted in FIG. 3. As shown in FIG. 5, embodiments of the method 500 may include receiving the second physiological signal (block 502); applying a heart sounds filter to the second physiological signal to create a filtered second physiological signal (block 504); and applying a temporal filter to the second physiological signal to determine a temporal window corresponding to a beat (block 506).

Embodiments of the method 500 further include identifying signal peaks within the temporal window (block 508); and extracting, from the filtered physiological signal, acceleration data corresponding to the identified signal peaks (block 510). In embodiments, the method 500 may further include identifying approximate heart sounds locations based on a template (block 512); and cross-correlating a number of extracted beats to the template (block 514). In embodiments, beat detection locations may be refined using an external global resolution clock (block 516).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A medical system for monitoring heart sounds of a subject, the system comprising:
   a medical device in wireless communication with a mobile device,
   the medical device is an implantable medical device and is configured to: (1) obtain, during a first sampling interval, a first physiological signal from a first accelerometer, (2) detect a quiet period, wherein the quiet period comprises a period of time that has a length that exceeds a specified threshold and during which an activity level of the subject satisfies a specified quiet condition, and (3) transmit a signal that is separate from the first physiological signal and that indicates that the quiet period has been detected,
   the mobile device comprising a second accelerometer and an analysis component,
   the analysis component is configured to cause the second accelerometer to obtain, during a second sampling interval, a second physiological signal only in response to receiving the signal indicating that the quiet period has been detected and extract heart sounds data from the second physiological signal.

2. The medical system of claim 1, wherein the analysis component is further configured to determine, based on the heart sounds data, at least one of heart rate, heart rate variability (HRV), and blood pressure.

3. The medical system of claim 1, further comprising a posture sensor implemented in the medical device and/or the mobile device, wherein the posture sensor is configured to determine a posture of the subject during the second sampling interval and provide an indication of the determined posture to the analysis component.

4. The medical system of claim 1, wherein the analysis component is configured to extract heart sounds data from the second physiological signal by:
   receiving the second physiological signal;
   applying a heart sounds filter to the second physiological signal to create a filtered second physiological signal;
   applying a temporal filter to the second physiological signal to determine a temporal window corresponding to a beat;
   identify signal peaks within the temporal window;
   extract, from the filtered physiological signal, acceleration data corresponding to the identified signal peaks; and
   determine, from the extracted acceleration data, the heart sounds data.

5. The medical system of claim 4, wherein the analysis component is configured to determine the heart sounds data by identifying approximate heart sounds locations based on a template and cross-correlating a plurality of extracted beats to the template.

6. The medical system of claim 1, wherein the analysis component is further configured to:
   determine a first timing fiducial extracted from the first physiological signal obtained by the medical device and a second timing fiducial extracted from the second physiological signal obtained by the mobile device;
   determine a difference between the first timing fiducial and the second timing fiducial; and
   determine, based on the difference, a blood pressure measurement.

7. The medical system of claim 1, further comprising a support device configured to communicate with the medical device and the mobile device and synchronize the medical device and the mobile device to a global resolution clock.

8. The medical system of claim 1, wherein the analysis component is configured to fork the second physiological signal to a first filter and a second filter.

9. The medical system of claim 1, wherein the analysis component is configured to apply a first filter to the second physiological signal to filter frequencies outside 10-90 hertz, wherein the analysis component is configured to apply a second filter, which is a temporal filter.

10. A method of monitoring heart sounds of a subject using a mobile phone and a medical device that is implantable, the method comprising:
    detecting, by a first acceleration sensor of the medical device, a quiet period comprising a period of time that has a length that exceeds a specified threshold and during which an activity level of the subject satisfies a specified quiet condition;
    outputting, by the medical device, a signal that is separate from a first physiological signal and that indicates that the quiet period had been detected;
    causing, in response to receiving the signal indicating the detected quiet period, the mobile phone to obtain a second physiological signal via a second acceleration sensor;
    applying a frequency filter to the second physiological signal to create a filtered physiological signal;
    applying a temporal filter to the second physiological signal to determine a temporal window corresponding to a beat;
    identifying signal peaks within the temporal window;
    extracting, from the filtered physiological signal, acceleration data corresponding to the identified signal peaks; and
    determining, from the extracted acceleration data, heart sounds data.

11. The method of claim 10, wherein determining the heart sounds data comprises:

identifying approximate heart sounds locations based on a template; and cross-correlating a plurality of extracted beats to the template.

12. The method of claim 10, further comprising:

determining a first timing fiducial and a second timing fiducial, wherein the first timing fiducial corresponds to a first beat extracted from the first physiological signal obtained by the medical device, and wherein the second timing fiducial corresponds to a second beat extracted from the first physiological signal obtained by the mobile phone;

determining a difference between the first timing fiducial and the second timing fiducial; and determining, based on the difference, a blood pressure measurement.

13. The method of claim 10, wherein the frequency filter filters frequencies outside 10-90 hertz.

14. The method of claim 13, wherein the temporal filter filters frequencies outside 0.5-2 hertz.

15. The method of claim 10, wherein the mobile phone is positioned adjacent the subject's thigh region.

* * * * *